US006444806B1

(12) United States Patent
Veerapanani et al.

(10) Patent No.: US 6,444,806 B1
(45) Date of Patent: Sep. 3, 2002

(54) CONJUGATES AND METHODS OF FORMING CONJUGATES OF OLIGONUCLEOTIDES AND CARBOHYDRATES

(75) Inventors: Dange Veerapanani, Lawrence, KS (US); Iwao Nozawa, Tokyo (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 08/837,651

(22) Filed: Apr. 22, 1997

Related U.S. Application Data (63) Continuation-in-part of application No. 08/640,263, filed on Apr. 30, 1996, now abandoned.

(51) Int. Cl.[7] .................. C07H 21/00; A01N 43/04; G01N 33/566
(52) U.S. Cl. .................. 536/25.3; 436/501; 514/44; 536/22.1; 536/23.1
(58) Field of Search ................ 435/6; 514/44; 436/501; 536/23.1, 22.1, 25.3

(56) References Cited

U.S. PATENT DOCUMENTS 5,578,718 A * 11/1996 Cook et al. ............ 536/27.21
5,977,084 A * 11/1999 Szoka, Jr. et al. ........... 514/44

OTHER PUBLICATIONS

*The Principles and Practice of Blood Grouping*, Edited by Erskine et al., [Publ. by The C.V. Mosby Company, Saint Louis, Missouri]pp. 57 and 58, 1973.*

Bonfils et al.; Drug targeting: synthesis and endocytosis of oligonucleotide–neoglycoprotein conjugates; Nucleic Acids Research, vol. 20, No. 17 4621–4629 (1992).

(List continued on next page.)

*Primary Examiner*—Ardin H. Marschel
(74) *Attorney, Agent, or Firm*—Hovey Williams LLP (57) ABSTRACT

Oligonucleotides conjugated to carbohydrates and methods for their production are described. These oligonucleotide-carbohydrate conjugates are resistant to degradation by nucleases, are able to form stable duplexes with RNA, and have utility as inhibitors of gene expression.

50 Claims, 4 Drawing Sheets

OTHER PUBLICATIONS

Shaw et al.; Modified deoxyoligonucleotides stable to exonuclease degradation in serum; Nucleic Acids Research, vol. 19, No. 4, 747 (1991).

Reed et al.; Acridine– and Cholesterol–Derivatized Solid Supports for Improved Synthesis of 3'–Modified Oligonucleotides; Bioconjugate Chem., 1991, 2, 217–225.

Brandley et al.; Carbohydrate Ligands of the LEC Cell Adhesion Molecules; Cell, vol. 63, 861–863 (1990).

Sanghvi et al.; Antisense oligodeoxynucleotides: synthesis, biophysical and biological evaluation of oligodeoxynucleotides containing modified pyrimidines, Nucleic Acids Res., vol. 21, #14, pp. 3197–3202 (1993).

Kawaski et al.; Uniformly Modified 2'–Deoxy–2'–fluoro phosphorothioate oligonucleotides as nuclease–resistant antisense compunds with high affinity and specificity for RNA targets; J. Med. Chem. 1993, 36, 831–841.

Tam et al.; Bilogical availability and nuclease resistance extend the in vitro activity of a phosphorothioate–3'–hydroxypropylamine oligonucleotide; Nucleic Acids Research, 1994, vol. 22, No. 6, 977–986.

Akhtar et al.; Stability of antisense DNA oligodeoxynucleotide analogs in cellular extracts and sera; Life Sciences, vol. 49, pp. 1793–1801 (1991).

Wood et al.; A novel method for the incorporation of glycoprotein–derived oligosaccharides into neoglycopeptides; Bioconjugate Chem., 1992, 3, 391–396.

Riva et al.; Protease–catalyzed regioselective esterification of sugars and related compounds in anhydrous dimethylformamide; J. Am Chem. Soc. 1998, 110, 584–589.

Patil et al.; Enzymatic Synthesis of a sucrose–containing linear polyester in nearly anhydrous organic media; Biotechnology and Bioengineering, vol. 37, pp. 639–646 (1991).

Khan et al.; A novel method to stabilise antisense oligonucleotides against exonuclease degradation; Nucleic Acids Research, 1993, vol. 21, No. 12 2957–2958.

Plank et al.; Gene transfer into hepatocytes using asialoglycoprotein receptor mediated endocytosis of DNA complexed with an artificial tetra–antennary galactose ligand; Bioconjugate Chem., 1992, 3, 533–539.

Ghosh et al.; Oligodeoxynucleotides as antisense inhibitors of gene expression; Progress in Nucleic Acid Research and Molecular Biology, vol. 42, pp. 79–127 (1992).

Sharon et al.; Lectins as cell recognition molecules; Science, vol. 246, Oct. 13, 1989, pp. 227–234.

X.Ma et al.; Design and synthesis of RNA miniduplexes via a synthetic linker approach; Nucleic Acids Research, 1993, vol. 21, No. 11, 2585–2589.

Chu et al.; The stability of different forms of double–stranded decoy DNA in serum and nuclear extracts; Nucleic Acids Research, vol. 20, No. 21, 5857–5858 (1992).

* cited by examiner

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iv) ANTI-SENSE: YES (xi) SEQUENCE DESCRIPTION: SEQ ID NO:1:

GCTTCTGTGC TCATGGTCT                                              19

CONJUGATES AND METHODS OF FORMING CONJUGATES OF OLIGONUCLEOTIDES AND CARBOHYDRATES

This is a continuation-in-part of identically titled application Ser. No. 08/640,263, filed Apr. 30, 1996 now abandoned.

BACKGROUND OF THE INVENTION

1. Field of the Invention

The present invention is broadly concerned with oligonucleotide-carbohydrate conjugates which are resistant to nuclease degradation and can be used as inhibitors of gene expression. More particularly, the invention pertains to such conjugates which are preferably formed using carbohydrates (e.g., sucrose) coupled via crosslinkers (e.g., 1,5-bis (succinimidooxycarbonyloxy)pentane) to the 3'-ends of oligonucleotides. The invention also relates to a method of inhibiting gene expression wherein a conjugate is transported into a cell where it can react with a macromolecule (e.g., mRNA and double-stranded DNA) to form a complex, and thus inhibit gene expression. Thus, these conjugates can be used as oligonucleotide drugs useful in treating diseases caused by the expression of specific genes.

2. Description of the Prior Art

Recent studies have indicated that oligonucleotides have potential therapeutic value. Oligonucleotides may act as antisense inhibitors of gene expression in a number of ways. Single-stranded oligodeoxynucleotides may arrest translation by forming heteroduplexes with mRNA, or may arrest transcription by forming triple-strand helices with duplex DNA. Catalytic ribonucleotides (ribozymes) may inhibit gene expression by cleaving complementary mRNAs. Furthermore, double-stranded oligonucleotides may bind to protein sites that recognize specific sequences of bases, thereby inhibiting polymerases. (Ghosh et al., *Progress in Nucleic Acid Research and Molecular Biology*, 42:79–126, 1992).

Two factors may limit the use of oligonucleotides as therapeutic agents. First, unmodified oligonucleotides are particularly susceptible to degradation by ubiquitous nucleases. Many of these nucleases exhibit 3' to 5' exonuclease activity and require a hydroxyl group at the 3'-end of the DNA molecule for activity. Second, the therapeutic action of oligonucleotides is limited by their low ability to enter the target cell.

Many approaches have been taken to limit the nuclease susceptibility of oligonucleotides. One approach has been to modify the phosphorous atom of the phosphodiester linkage to produce phosphorothioates, methylphosphorates, and phosphoramidates. (Uhlamann et al., *Chem. Rev.*, 90:543–584,1990; Goodchild, *Bioconjugate Chem.*, 1:165–186, 1990). Although this approach has given significant resistance to nuclease degradation, the ability of the oligonucleotide to support RNase-mediated degradation of RNA is compromised. (Dagel et al., *Antisense Res. Develop.*, 1:11–20, 1991). RNase H is a nuclease which degrades only RNA that is hybridized to DNA and is commonly used to gauge the ability of an oligodeoxynucleotide to form a stable duplex with RNA. However, phosphorothioate oligonucleotides incorporating 2'-deoxy-2'-fluoroadenosine, -guanosine, -uridine, and -cytidine did enhance duplex stability as measured by melting temperature ($T_m$) without compromising base-pair specificity. (Kawasaki et al., *J. Med. Chem.*, 36:831–841, 1993).

Terminal phosphorothioate and methane phosphorate modifications were shown to protect an oligonucleotide from exonucleases such as snake venom phosphodiesterase and spleen phosphodiesterase. (Stein et al., *Nucleic Acids Research*, 16:3209–3221, 1988; Agrawal et al., *Tetrahedron Lett.*, 27:5575–5578, 1986). Additionally, terminal methane phosphonate modifications were useful in protecting oligodeoxynucleotides from nuclease digestion in fetal calf serum. (Tidd et al., *Br. J. Cancer*, 60:343, 1989).

Modification of pyrimidines at their 5- and/or 6-positions resulted in enhanced nuclease stability of deoxyoligonucleotides in fetal calf serum and did not inhibit RNase H-mediated degradation of RNA. (Sanghvi et al., *Nucleic Acids Research*, 21:3197–3203, 1993). Also, deoxyoligonucleotides modified at the 3'- and/or 5'-terminal phosphate with phosphoroamidate linkages blocked exonucleolytic degradation in human serum, fetal calf serum, and cell media; furthermore, these terminal modifications maintained high binding affinity of the oligonucleotide for the complementary DNA sequence as shown by thermal denaturation measurements. (Shaw et al., *Nucleic Acids Research*, 19:747–750, 1991).

The inclusion of an 8 base-pair sequence encoding a hairpin loop on the 3' end effectively stabilized a deoxyoligonucleotide against degradation by phosphodiesterase-1 and in fetal calf serum. Thermal denaturation experiments showed that the $T_m$ of this oligonucleotide hybridized to its complementary mRNA was unaffected by the presence of the secondary structure modification. (Kahn et al., *Nucleic Acids Research*, 21:2957–2958, 1993).

An oligonucleotide containing internucleotide phosphorothioates and 3' alkylamine exhibited in vitro stability to nucleases in fetal calf serum and in cell culture. Additionally, treatment of HeLa cells with this oligonucleotide inhibited expression of the target gene 15 days following initial oligonucleotide treatment. Confocal microscopy revealed that an oligonucleotide with both modifications exhibited greater accumulation and release from cytoplasmic vesicles compared to an oligonucleotide containing only the 3' alkylamine addition. Increased intracellular accumulation and distribution of oligonucleotides are factors known to affect their biological availability. (Tam et al., *Nucleic Acids Research*, 22:977–986, 1994).

Although the studies described above demonstrate that specific modifications of oligonucleotides result in enhanced resistance to nucleases, these investigations have not linked oligonucleotide modifications to improved methods of cellular uptake. Unfortunately, little is known about the interaction of oligonucleotides with cell membranes.

Letsinger et al., *Proc. Natl. Acad. Sci. USA*, 86:6553–6556, 1989, linked a cholesteryl group to the 3'-terminal internucleotide phosphorus of phosphodiester and phosphorothioate oligonucleotides in order to increase oligonucleotide solubility in cell membranes. These compounds significantly inhibited replication of human immunodeficiency virus (HIV) in tissue culture.

The presence of polylysine at the 3'-end of oligonucleotides complementary to the HIV-1 splice donor site resulted in a significant reduction in the production of viral structural proteins and virus tissue in infected cultures. (Stevenson et al., *J. Gen. Virol.*, 70:2673–2682, 1989). The authors postulated that the alteration in lipid solubility imparted by an attached polylysine moiety affects both the ability of an oligonucleotide to cross the cell membrane and its intracellular distribution.

Recently, gene-transfer methods have been developed that exploit natural receptor-mediated endocytosis pathways for the delivery of DNA into cells. One such class of receptors are the lectins, which specifically recognize carbohydrate residues. Ligands for cell receptors such as asialorosomucoid (Wu et al., *J. Biol. Chem.*, 262:4429–4432, 1987), albumin-bound insulin (Huckett et al., *Biochem. Pharmacol.*, 40:253–263, 1990), transferrin (Wagner et al., *Proc. Natl. Acad. Sci. USA*, 87:3410–3414, 1990), and viral proteins (Cotten et al., *Methods Enzymol.*, 217:618–644, 1992) have been successfully used to import DNA molecules into cells. In each case, the ligand was conjugated to DNA-binding protein and incubated with DNA. Resultant ligand-coated DNA was able to bind to receptors on the cell surface and was subsequently internalized.

Drawbacks of this approach include the difficulty of controlling the protein conjugation chemistry (Plank et al., *Bioconjugate Chem.*, 3:533–539, 1992), and limited gene delivery due to accumulation of DNA complexes in intracellular vesicles. Zatloukal et al., *Ann. N.Y. Acad. Sci.*, 660:136–153, 1992). Cotten et al., *Proc. Natl. Acad. Sci. USA*, 87:4033–4037,1990, have attempted to overcome these problems by replacing large protein ligands with smaller compounds that mimic ligand-binding to a receptor. These researchers constructed an artificial ligand for the asialoglycoprotein which contained four terminal galactose residues on a branched carrier peptide. This synthetic ligand was conjugated to polylysine-bound DNA and delivered into cultured hepatocytes.

Bonfils et al., *Nucleic Acids Research*, 20:4621–4629, 1992, covalently linked an oligonucleotide substituted at the 3'-end by a thiol group to 6-phosphomannosylated bovine serum albumin via a disulfide bridge. The conjugated oligonucleotide was stable in fetal bovine serum. The cellular uptake of the conjugation was mediated by mannose-6-phosphate membrane lectins.

Thus, the prior art reveals the difficulties researchers have encountered in developing efficient methods of delivery of oligonucleotides into cells in order to inhibit expression of specific genes.

SUMMARY OF THE INVENTION

The present invention provides an essential step in oligonucleotide therapy: the efficient delivery of oligonucleotides into cells. In this invention, an oligonucleotide is conjugated to a carbohydrate. The preferred on conjugates os the invention include (and more preferably consist essentially of) a single oligonucleotide compound conjugated to a carbohydrate with a crosslinker, as these species are herein defined. The carbohydrate of the conjugate has two roles. It may act as a ligand which can recognize a specific receptor located at the surface of the target cell. Receptor-bound conjugate then may be transported into the cell by receptor-mediated endocytosis. Furthermore, the carbohydrate of the conjugate protects the covalently attached oligonucleotide from attack by nucleases. The present invention is unique and unknown in the prior art in that no one has conjugated a nucleic acid molecule directly to a carbohydrate molecule in order to facilitate transport across cell membranes or to protect an oligonucleotide from degradation by nucleases.

In the most preferred embodiment, the oligonucleotide-carbohydrate conjugate is formed by covalently attaching a sucrose molecule to the 3'-end hydroxyl group of either a phosphodiester or phosphorothioate oligodeoxynucleotide via the crosslinker 1,5-bis(succinimidooxycarbonyloxy)-pentane. The oligonucleotide has a length of at least about 2 nucleotides, ideally from about 2 to 50 nucleotides. The conjugate is synthesized in reactions catalyzed by Bacillus protease type VIII (subtilisin); these reactions are carried out in anhydrous pyridine at from about 35 to 60° C., ideally from about 40 to 50° C., for 24 hours in a single reaction mixture with agitation of reactants. The resultant sucrose-conjugated oligonucleotides are resistant to degradation by Exonuclease-1 and by endogenous nucleases present in fetal calf serum. Furthermore, attachment of sucrose does not destroy the capacity of the oligonucleotides to form stable duplexes with RNA, since such duplexes are able to support RNase H-mediated degradation of the RNA strand.

However, the oligonucleotide, carbohydrate, crosslinker, and enzyme used in the synthesis of the conjugate are not limited to oligodeoxynucleotides, sucrose, 1,5-bis(succinimidooxycarbonyloxy)pentane, and subtilisin, respectively. Suitable oligonucleotides also include oligoribonucleotides, both catalytic (ribozymes) and uncatalytic. Selection of a carbohydrate depends upon the receptor utilized in cellular uptake of the oligonucleotide; suitable carbohydrates include sucrose, N-acetyllactosamine, galactose, glucose, mannose, Sialyl Lewis$^x$ and derivatives and fragments thereof, and carbohydrate moieties of biofunctional glycoproteins and glycopeptides having amino acid residue lengths of up 10 amino acid residues. The most preferred carbohydrates have high cell receptor binding capacities, such as sucrose, mannose and galactose. Suitable crosslinkers include the following compounds:

wherein each R moiety is a succinimidyl, imidazolyl, benzoimidazolyl, triazolyl, or maleimidyl moiety, and each n equals from 1 to 50. Suitable enzymes include Bacillus protease bioenzyme 240, Bacillus protease B-500, alkaline protease, aminoacylase, and lipase. The invention also comprehends attachment of the carbohydrate to the oligonucleotide without the use of a crosslinker or enzyme. Those of ordinary skill in the art recognize that the conjugate can be formed in a nonenzymatic chemical reaction.

As used herein, "carbohydrate" refers to a compound which is either a carbohydrate per se made up of one or more monosaccharide units having at least 6 carbon atoms (which may be linear, branched or cyclic) with an oxygen atom bonded to each carbon atom; or a compound having as a part thereof a carbohydrate moiety made up of one or more monosaccharide units each having at least six carbon atoms (which may be linear, branched or cyclic), with an oxygen atom bonded to each carbon atom. Generally, the preferred carbohydrates useful in the invention are of relatively low molecular weight in order to minimize the changes of the final conjugant being immunogenic in vivo; the selected carbohydrate per se or carbohydrate moiety-containing compound should therefore preferably have a molecular weight of up to about 1,500 and more preferably up to about 500. Representative carbohydrates include the sugars (mono-, di-, tri-, and oligosaccharides containing from about 4–9 monosaccharide units), and polysaccharides such as starches, glycogen, cellulose and polysaccharide gums. Specific monosaccharides include $C_6$ and above (preferably $C_6$–$C_8$) sugars such as glucose, fructose, mannose, galactose and sedoheptulose; di- and trisaccharides would include sugars having two or three monosaccharide units (preferably $C_5$–$C_8$) such as sucrose, cellobiose, maltose, lactose, and raffinose.

On the other hand, an "oligonucleotide" is a compound made up of recurring nucleotide units, each consisting of a nitrogenous base, a 5-carbon sugar moiety (ribose in RNA and deoxyribose in DNA). An oligonucleotide is not a "carbohydrate" in the context of the present invention, which requires one or more $C_6$ or greater monosaccharide units therein. In addition, oligonucleotides are characterized by specific recurrent nitrogenous basis (adenine, guanine, cytosine, uracil or thymine referred to as A, G, C, U and T respectively), and phosphodiester linkages. Preferably, the carbohydrates of the invention are essentially or completely free of both the characterizing A, G, C, U and T nitrogeneous bases and/or phosphodiester conjugation linkages between the carbohydrate and oligonucleotide.

The preferred oligonucleotide-carbohydrate conjugates of the invention should be non-proteinaceous, i.e., free of protein or peptide-like moieties having over 10 amino acid residues. Neither the oligonucleotide, the carbohydrate nor the crosslinker should therefore contain an amino acid residue moiety exceeding 10 amino acid residues in length.

The preferred class of crosslinkers includes non-naturally occurring, non-proteinaceous synthetic compounds having a molecular weight of up to 20,000 (preferably up to 10,000) and which are electrically neutral. The crosslinkers should therefore not be in the form of large proteinaceous compounds of high molecular weight and electrical charge. In the most preferred form, the molecular weight of the crosslinker should be less than, and certainly no more than, that of the oligonucleotide. In the more general case, the molecular weight of the cross linker should not be greater than two times the molecular weight of the oligonucleotide.

An oligonucleotide-carbohydrate conjugate, once transported into the target cell, may inhibit gene expression by binding to a cellular macromolecule (e.g., mRNA and double-stranded DNA) to form a complex. Thus, the oligonucleotide may hybridize to complementary mRNA, resulting in either translation arrest or degradation of the mRNA by RNase H. If the oligonucleotide is a ribozyme, it may cleave the mRNA. Alternately, the oligonucleotide may hybridize to double-stranded DNA, resulting in transcription arrest. Thus, the conjugates of the present invention may serve as therapeutic agents useful in treating diseases resulting from expression of specific genes.

DETAILED DESCRIPTION OF THE PREFERRED EMBODIMENT

It is to be understood that these examples are set forth by way of illustration only, and nothing therein shall be taken as a limitation upon the overall scope of the invention.

The following examples describe (1) a method for the preparation of antisense oligonucleotides conjugated at their 3'-ends to sucrose, and (2) a series of experiments undertaken to test the stability and hybridization properties of these oligonucleotides.

EXAMPLE 1

Polyacrylamide Gel Electrophoresis

Electrophoresis was performed using 20% polyacrylamide gels containing 7% urea, 90 mM Tris-borate (pH 8.3), 2 mM EDTA, 0.02% ammonium persulfate, and 15 µl tetraethylediamine (TEMED). Samples were dissolved in gel-loading buffer (10 M urea, 1.5 mM EDTA, 0.05% xylene cyanol, and 0.05% bromophenol blue) and heated at 90° C. for 1 minute and chilled before application to polyacrylamide gels.

EXAMPLE 2

Synthesis of Oligonucleotides

Both phosphodiester and phosphorothioate oligonucleotides used in this study were 19 nucleotides in length and had the nucleotide sequence presented in Sequence ID No. 1. The phosphodiester 19-mer was synthesized by standard phosphoramadite chemistry on a 392 DNA synthesizer (Applied Biosystems, Foster City, Calif.). Phosphodiester oligonucleotide was converted to phosphorothioate oligonucleotide by sulfurization using tetraethylthiuram disulfide (TETD) reagent (Applied Biosystems, Foster City, Calif.). Following deprotection and cleavage from the column support by ammonium hydroxide, the oligonucleotides were purified from 20% polyacrylamide gels by electroelution followed by ethanol precipitation. Complementary ribonucleotide 30 nucleotides in length was custom-synthesized by Genset (San Diego, Calif.).

EXAMPLE 3
Radiolabeling of Oligonucleotides

Oligonucleotide was incubated with 10 units of T4 polynucleotide kinase (Promega, Madison, Wis.) per µg of oligonucleotide in 50 mM Tris-HCl (pH 7.6), 5 mM $MgCl_2$, 100 mM dithiothreitol, 1 mM ATP, and 20 µCi $\gamma$-$^{32}$P-dATP in 50 µl for 90 minutes at 37° C. Unincorporated $^{32}$P-labeled ATP was removed using a sephadex G-25 column and radiolabeled oligonucleotide was precipitated with ethanol.

EXAMPLE 4
Preparation of Sucrose-Conjugated Oligonucleotide

Anhydrous pyridine (Aldrich Chemical Co., Milwaukee, Wis.) was dried over 3 Å molecular sieves for 24 hours prior to use. Subtilisin (EC 3.4.21.14, protease from *Bacillus subtilin;* Sigma Chemical Co., St. Louis, Mo.) was dissolved in 0.1 M Tris-HCl (pH 7.5), and lyophilized prior to use. One mg of oligonucleotide was added to 10 ml of pyridine containing 0.1 mM sucrose and 0.1 mM 1,5-bis (succinimidooxycarbonyloxy)pentane (Fluka, USA). The reaction was initiated by adding 150 mg of subtilisin. The suspension was shaken at 150 rpm at 45° C. for 24 hours. The reaction was terminated by filtering off the enzyme or by pelleting the sucrose-conjugated oligonucleotide by microcentrifugation at maximum speed. Sucrose-conjugated oligonucleotide was further purified by polyacrylamide gel electrophoresis.

EXAMPLE 5
Exonuclease-1 Degradation Assay

Radiolabeled oligonucleotide (30,000 CPM) was incubated with either 0.5 or 1.0 unit of Exonuclease-1 in 67 mM glycine (pH 9.5), 10 mM 2-mercaptoethanol, and 6.7 mM $MgCl_2$ in 20 µl for 30 minutes at 37° C. After incubation, 5 µl of gel-loading buffer were added. All reactions were analyzed by polyacrylamide gel electrophoresis followed by autoradiography of the wet gel at −70° C.

EXAMPLE 6
Nuclease Degradation Assay

Radiolabeled oligonucleotide (30,000 CPM) was incubated in RPMI-1640 medium (GIBCO-BRL, Grand Island, N.Y.) containing 10% heat-inactivated fetal bovine serum at 37° C. Samples were removed at various times, mixed with gel-loading buffer, and frozen at −20 C. Samples were analyzed by polyacrylamide gel electrophoresis followed by autoradiography of the wet gel at −70° C.

EXAMPLE 7
RNase H Assay

Radiolabeled oligonucleotide (30,000 CPM) was annealed to complementary RNA by incubation in 20 mM Tris-HCl (pH 7.5), 0.1 M KCl, 10 mM $MgCl_2$, and 0.1 mM ATP in 10 µl for 5 minutes at 65° C. followed by slow cooling to room temperature. One unit of *Escherichia coli* RNase H was added and incubation at room temperature was continued for either 10 minutes or 30 minutes. After incubation, 5 µl of gel-loading buffer were added, and all samples were analyzed by polyacrylamide gel electrophoresis followed by autoradiography of the wet gel at −70° C.

RESULTS AND DISCUSSION
Conjugation of Sucrose to the Oligonucleotides

Figure 1:
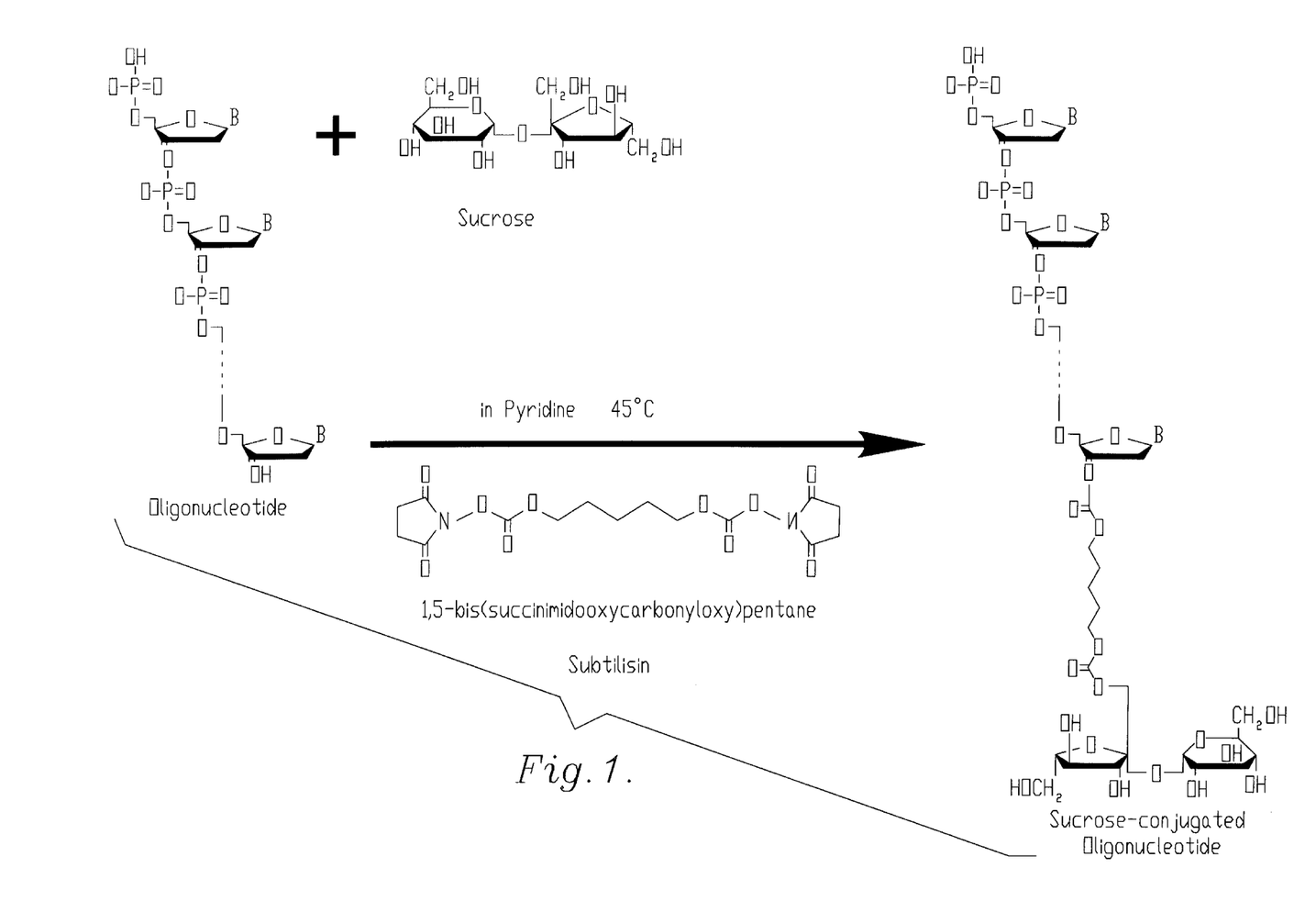
FIG. 1 depicts the enzyme-catalyzed reaction in which the 3'-end hydroxyl group of an oligonucleotide is coupled to sucrose by the crosslinker 1,5-bis(succinimidooxycarbonyloxy)pentane by *Bacillus subtilis* protease (type VIII) in the presence of anhydrous pyridine.
Figure 2:
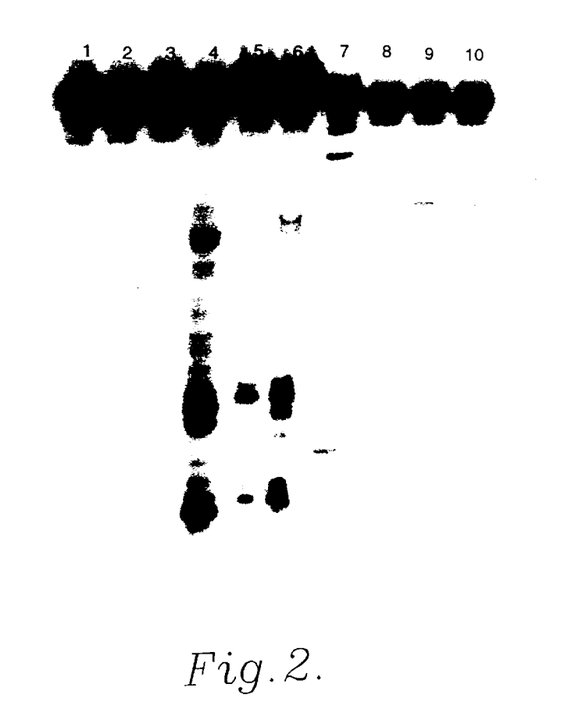
FIG. 2 depicts an autoradiogram of a polyacrylamide gel demonstrating the relative mobility of unconjugated radiolabeled oligonucleotide (lane 4) and sucrose-conjugated radiolabeled oligonucleotide (lane 5) (lanes 1 through 3 and 6 through 10 are irrelevant)
Figure 3:
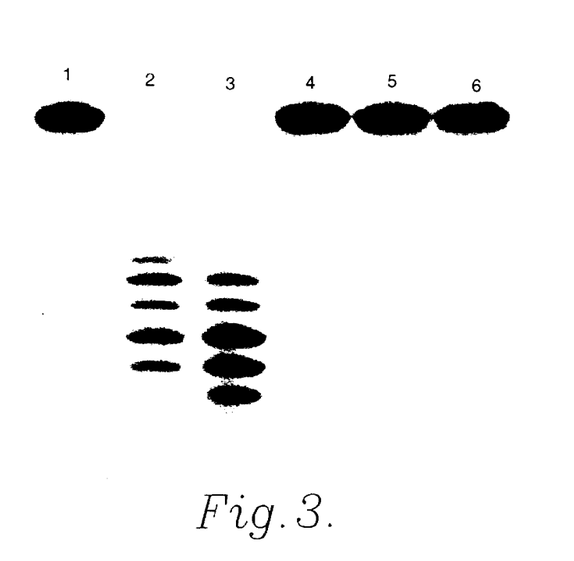
FIG. 3 depicts an autoradiogram of a polyacrylamide gel demonstrating degradation of unconjugated radiolabeled oligonucleotide with 0, 0.5, and 1.0 units of Exonuclease-1 (lanes 1 through 3, respectively), and sucrose-conjugated radiolabeled oligonucleotide with 0, 0.5, and 1.0 units of Exonuclease-1 (lanes 4 through 6, respectively)
Figure 4:
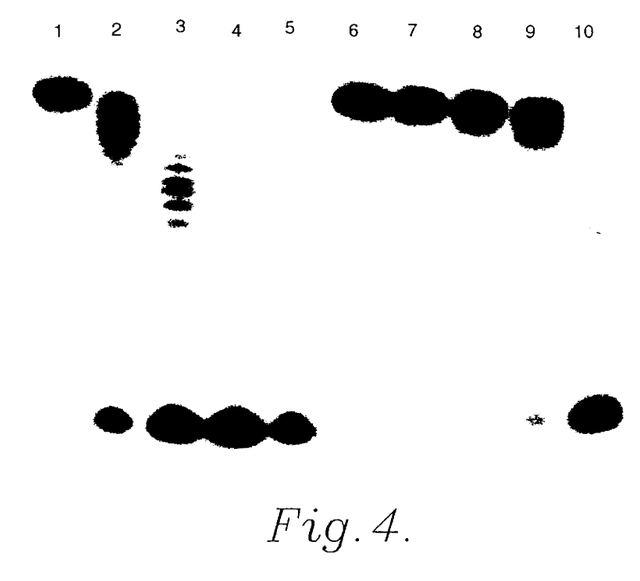
FIG. 4 depicts an autoradiogram of a polyacrylamide gel demonstrating nuclease degradation using heat-inactivated 10% fetal bovine serum of unconjugated radiolabeled phosphodiester oligonucleotide at 0, 0.15, 0.5, 2.0, and 24 hours of incubation (lanes 1 through 5, respectively), and sucrose-conjugated radiolabeled phosphodiester oligonucleotide at 0, 0.1, 0.5, 2.0, and 24 hours of incubation (lanes 6 through 10, respectively)

Sucrose-conjugated oligonucleotide appeared as one major band in an autoradiogram of a polyacrylamide gel, indicating that the purification of the compound resulted in very little degradation (FIG. 2, lane 5). Furthermore, the sucrose-conjugated oligonucleotide migrated more slowly in the polyacrylamide gel than the unconjugated oligonucleotide (FIG. 2, lane 4) because of the presence of a crosslinker and carbohydrate moiety at the 3'-end of the oligonucleotide.
Resistance of the Sucrose-Conjugated Oligonucleotide to Exonuclease-1 Degradation Unconjugated and sucrose-conjugated oligonucleotides were labeled at the 5'-end using $\gamma$-$^{32}$P-ATP and T4 polynucleotide kinase. These oligonucleotides were subject to digestion by different concentrations of Exonuclease-1 (FIG. 3). The unconjugated oligonucleotide was degraded nearly completely by Exonuclease-1 (FIG. 3, lanes 2 and 3), while sucrose-conjugated oligonucleotide exhibited only negligible degradation by Exonuclease-1 (FIG. 3, lanes 5 and 6).
Resistance of the Sucrose-Conjugated Oligonucleotide to Degradation in Heat-Inactivated 10% Fetal Bovine Serum Unconjugated and sucrose-conjugated 5'-$^{32}$P-labeled oligonucleotides were subject to degradation in heat-inactivated 10% fetal bovine serum for different amounts of time (FIG. 4). Unconjugated oligonucleotide was highly susceptible to degradation in fetal bovine serum (FIG. 4, lanes 2 through 5) while sucrose-conjugated oligonucleotide was relatively resistant to degradation in fetal bovine serum (FIG. 4, lanes 7 through 10).

Figure 5:
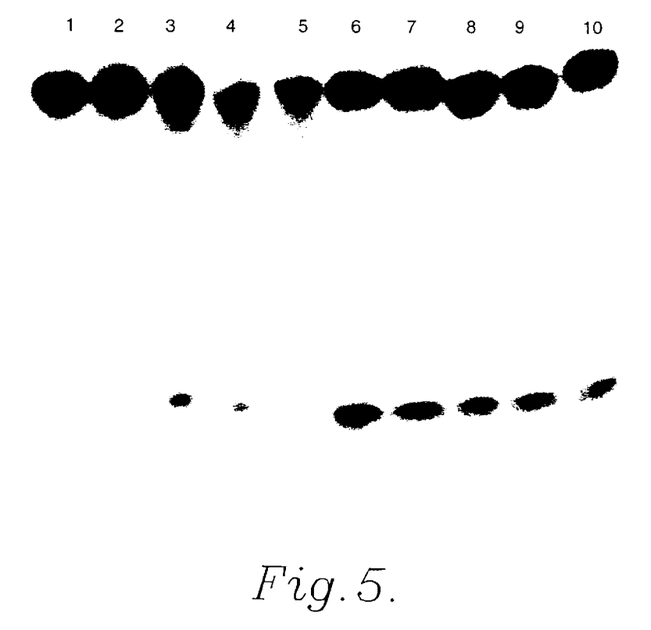
FIG. 5 depicts an autoradiogram of a polyacrylamide gel demonstrating nuclease degradation using heat-inactivated 10% fetal bovine serum of unconjugated radiolabeled phosphorothioate oligonucleotide for 0, 0.5, 2.0, 24, and 48 hours of incubation (lanes 1 through 5, respectively), and sucrose-conjugated radiolabeled phosphorothioate oligonucleotide for 0, 0.5, 2.0, 24, and 48 hours of incubation (lanes 6 through 10, respectively)
Figure 6:
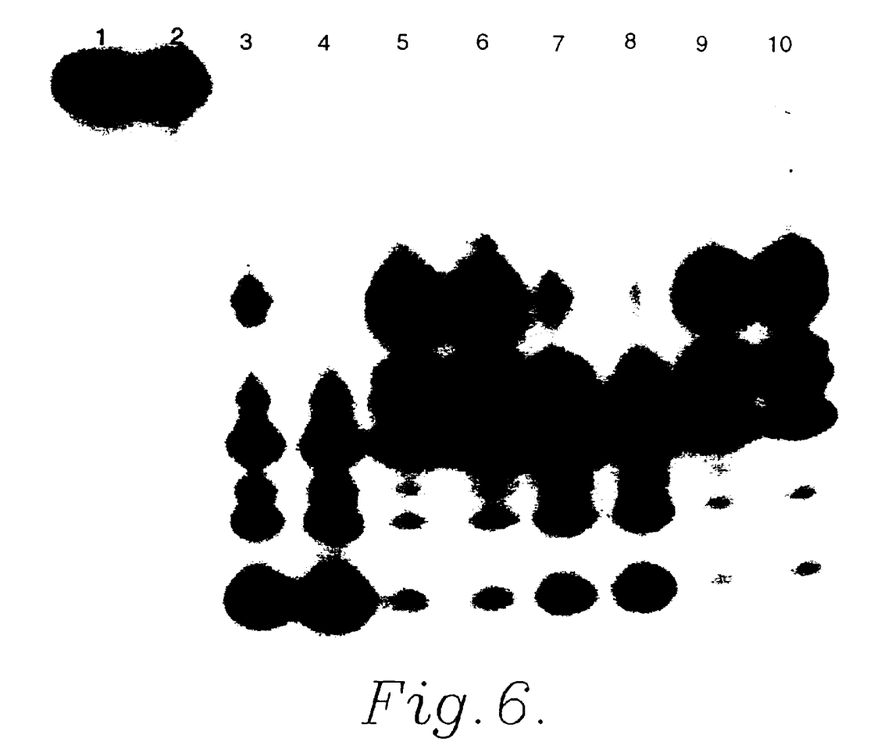
FIG. 6 depicts an autoradiogram of a polyacrylamide gel demonstrating hydrolysis by RNase H of radiolabeled RNA hybridized to no oligonucleotide at 0 and 10 minutes of incubation (lanes 1 and 2, respectively), unconjugated phosphodiester oligonucleotide at 10 and 30 minutes of incubation (lanes 3 and 4, respectively), sucrose-conjugated phosphodiester oligonucleotide at 10 and 30 minutes of incubation (lanes 5 and 6, respectively), unconjugated phosphorothioate oligonucleotide at 10 and 30 minutes of incubation (lanes 7 and 8, respectively), and sucrose-conjugated phosphorothioate oligonucleotide at 10 and 30 minutes of incubation (lanes 9 and 10, respectively).

Similarly, the sucrose-conjugated phosphorothioate oligonucleotide was more resistant to degradation in heat-inactivated 10% fetal bovine serum (FIG. 5, lanes 7 through 10) than unconjugated phosphorothioate oligonucleotide (FIG. 5, lanes 2 through 5).
Hybridization of Sucrose-Conjugated Oligonucleotides to RNA Unconjugated and sucrose-conjugated phosphodiester and phosphorothioate oligonucleotides were tested for their ability to form stable RNA-DNA heteroduplexes by determining RNA susceptibility to degradation by RNase H. RNA complementary to the oligonucleotide was labeled at the 5'-end using $\gamma$-$^{32}$P-ATP and T4 polynucleotide kinase. Radiolabeled RNA was hybridized to either unconjugated phosphodiester, sucrose-conjugated phosphodiester, unconjugated phosphorothioate, or sucrose-conjugated phosphorothioate oligonucleotide. Heteroduplex formation was assayed by incubation with RNase H for either 10 minutes or 30 minutes. In all cases, radiolabeled RNA that was hybridized to oligonucleotide was degraded by RNase H (FIG. 6), indicating that the sucrose moiety did not destroy the capacity of oligonucleotide to form stable heteroduplexes.

What is claimed is:

1. A conjugate having an oligonucleotide and sucrose coupled thereto by a crosslinker interposed between said oligonucleotide and said sucrose, said crosslinker comprising a non-naturally occurring, non-proteinaceous, electrically neutral synthetic compound having a molecular weight of up to about 20,000.

2. The conjugate of claim 1, wherein said oligonucleotide is selected from the group consisting of phosphodiester and phosphorothioate oligonucleotides.

3. The conjugate of claim 1, wherein said oligonucleotide is an oligodeoxynucleotide.

4. The conjugate of claim 1, wherein said oligonucleotide is an oligoribonucleotide.

5. The conjugate of claim 4, wherein said oligoribonucleotide is catalytic.

6. The conjugate of claim 1, wherein said oligonucleotide is at least about 2 nucleotides in length.

7. The conjugate of claim 6, wherein said oligonucleotide is from about 2 to 50 nucleotides in length.

8. The conjugate of claim 1, wherein said crosslinker is selected from the group consisting of:

wherein each R moiety is selected from the group consisting of succinimidyl, imidazolyl, benzoimidazolyl, triazolyl, and maleimidyl moieties, and each n equals from 1 to 50.

9. The conjugate of claim 8, wherein said crosslinker is 1,5-bis(succinimidooxycarbonyloxy)pentane.

10. The conjugate of claim 1, wherein said conjugate is useful in treating a disease caused by the expression of a specific gene.

11. A complex comprising a conjugate having an oligonucleotide and a carbohydrate coupled thereto by a crosslinker interposed between said oligonucleotide and said carbohydrate, said crosslinker being 1,5-bis (succinimidooxycarbonyloxy) pentane, wherein said conjugate is bound to a macromolecule selected from the group consisting of mRNA and double-stranded DNA.

12. The complex of claim 11, wherein said conjugate is bound to mRNA.

13. The complex of claim 11, wherein said oligonucleotide is selected from the group consisting of phosphodiester and phosphorothioate oligonucleotides.

14. The complex of claim 11, wherein said oligonucleotide is an oligodeoxynucleotide.

15. The complex of claim 11, wherein said oligonucleotide is an oligoribonucleotide.

16. The complex of claim 15, wherein said oligoribonucleotide is catalytic.

17. The complex of claim 11, wherein said oligonucleotide is at least about 2 nucleotides in length.

18. The complex of claim 17, wherein said oligonucleotide is from about 2 to 50 nucleotides in length.

19. The complex of claim 11, wherein said carbohydrate is selected from the group consisting of sucrose, N-acetyllactosamine, galactose, glucose, mannose, Sialyl Lewis$^x$ and derivatives and fragments thereof, and carbohydrate moieties of biofunctional glycoproteins and glycopeptides.

20. The complex of claim 19, wherein said carbohydrate is sucrose.

21. The complex of claim 11, wherein said carbohydrate is coupled to the 3'-end of said oligonucleotide.

22. A method of forming a conjugate having an oligonucleotide and a carbohydrate coupled thereto, including the steps of:
    providing an oligonucleotide, a carbohydrate and a crosslinker comprising a non-naturally occurring, non-proteinaceous, electrically neutral synthetic compound having a molecular weight of up to about 20,000; and reacting said oligonucleotide with said carbohydrate and crosslinker to form said conjugate, said reacting step being catalyzed by an enzyme.

23. The method of claim 22, wherein said enzyme is selected from the group consisting of Bacillus protease type VIII, Bacillus protease bioenzyme 240, Bacillus protease B-500, alkaline protease, aminoacylase, and lipase.

24. The method of claim 23, wherein said enzyme is Bacillus protease type VIII.

25. The method of claim 22, wherein said reacting step is conducted at a temperature of from about 35 to 600° C.

26. The method of claim 25, wherein said reacting step is conducted at a temperature of from about 40 to 50° C.

27. The method of claim 22, wherein reactants are agitated in said reacting step.

28. The method of claim 22, wherein said oligonucleotide is selected from the group consisting of phosphodiester and phosphorothioate oligonucleotides.

29. The method of claim 22, wherein said oligonucleotide is an oligodeoxynucleotide.

30. The method of claim 22, wherein said oligonucleotide is an oligoribonucleotide.

31. The method of claim 30, wherein said oligoribonucleotide is catalytic.

32. The method of claim 22, wherein said oligonucleotide is at least about 2 nucleotides in length.

33. The method of claim 32, wherein said oligonucleotide is from about 2 to 50 nucleotides in length.

34. The method of claim 22, wherein said carbohydrate is selected from the group consisting of sucrose, N-acetyllactosamine, galactose, glucose, mannose, Sialyl Lewis$^x$ and derivatives and fragments thereof, and carbohydrate moieties of biofunctional glycoproteins and glycopeptides.

35. The method of claim 34, wherein said carbohydrate is sucrose.

36. The method of claim 22, wherein said carbohydrate is coupled to the 3'-end of said oligonucleotide.

37. The method of claim 22, wherein said crosslinker is selected from the group consisting of:

[chemical structures]

wherein each R moiety is selected from the group consisting of succinimidyl, imidazolyl, benzoimidazolyl, triazolyl, and maleimidyl moieties, and each n equals from 1 to 50.

38. The method of claim 37, wherein said crosslinker is 1,5-bis(succinimidooxycarbonyloxy)pentane.

39. The conjugate of claim 1, said conjugate consisting essentially of a single oligonucleotide molecule with said sucrose coupled thereto by a crosslinker interposed between said oligonucleotide and said sucrose, said crosslinker comprising a non-naturally occurring, non-proteinaceous, electrically neutral synthetic compound having a molecular weight of up to about 20,000.

40. The complex of claim 11, said conjugate consisting essentially of a single oligonucleotide molecule with said carbohydrate coupled thereto.

41. The complex of claim 40, including a crosslinker coupling said oligonucleotide molecule and said carbohydrate.

42. The complex of claim 11, said carbohydrate having a molecular weight of up to about 1500, there being a crosslinker coupling said oligonucleotide and said carbohydrate, said crosslinker being electrically neutral and having a molecular weight of up to about 20,000.

43. A conjugate having an oligonucleotide and a carbohydrate coupled thereto by a crosslinker interposed between said oligonucleotide and said carbohydrate, said crosslinker being 1,5-bis(succinimidooxycarbonyloxy) pentane.

44. A complex comprising a conjugate having an oligonucleotide and sucrose coupled thereto by a crosslinker interposed between said oligonucleotide and said sucrose, said crosslinker comprising a non-naturally occurring, non-proteinaceous, electrically neutral synthetic compound having a molecular weight of up to about 20,000 wherein said conjugate is bound to a macromolecule selected from the group consisting of mRNA and double-stranded DNA.

45. A method of forming a conjugate having an oligonucleotide and sucrose coupled thereto, including the steps of:

providing an oligonucleotide, sucrose, and a crosslinker comprising a non-naturally occurring, non-proteinaceous electrically neutral synthetic compound having a molecular weight of up to about 20,000; and reacting said oligonucleotide with said sucrose and crosslinker to form said conjugate.

46. A method of forming a conjugate having an oligonucleotide and a carbohydrate coupled thereto, including the steps of:

providing an oligonucleotide a carbohydrate and a crosslinker comprising a non-naturally occurring, non-proteinaceous, electrically neutral synthetic compound having a molecular weight of up to about 20,000; and reacting said oligonucleotide with said carbohydrate and crosslinker to form said conjugate, said crosslinker being 1,5-bis(succinimidooxycarbonyloxy) pentane.

47. A conjugate having an oligonucleotide presenting opposed terminal 3' and 5' ends and a sugar comprising sucrose coupled thereto by a crosslinker interposed between said oligonucleotide and said sugar, neither said sugar, oligonucleotide, nor crosslinker containing an amino acid residue moiety exceeding 10 amino acid residues in length, said crosslinker comprising a non-naturally occurring, non-proteinaceous, electrically neutral synthetic compound having a molecular weight of up to about 20,000, and said crosslinker being covalently coupled to one of said oligonucleotide ends.

48. A complex comprising a conjugate having an oligonucleotide presenting opposed 3' and 5' terminal ends, and a sugar comprising sucrose coupled thereto by a crosslinker interposed between said oligonucleotide and said sugar, neither said sugar, oligonucleotide, nor crosslinker containing an amino acid residue moiety exceeding 10 amino acid residues in length, said crosslinker comprising a non-naturally occurring, non-proteinaceous, electrically neutral synthetic compound having a molecular weight of up to about 20,000, wherein said conjugate is bound to a macromolecule selected from the group consisting of mRNA and double-stranded DNA, said crosslinker being covalently coupled to one of said oligonucleotide ends.

49. A method of forming a conjugate having an oligonucleotide and a sugar coupled thereto, including the steps of:

providing an oligonucleotide presenting opposed 3' and 5' terminal ends, a sugar comprising sucrose and a crosslinker comprising a non-naturally occurring, non-proteinaceous, electrically neutral synthetic compound having a molecular weight of up to about 20,000; and reacting said oligonucleotide with said sugar and crosslinker to form said conjugate, said crosslinker being covalently coupled to one of said oligonucleotide ends, neither said sugar, oligonucleotide, nor crosslinker containing an amino acid residue moiety exceeding 10 amino acid residues in length.

50. The conjugate of claim 1, wherein said sucrose is coupled to the 3'-end of said oligonucleotide.

* * * * *